US00PP34410P2

(12) United States Plant Patent
Post

(10) Patent No.: US PP34,410 P2
(45) Date of Patent: Jul. 5, 2022

(54) ***CHRYSANTHEMUM* PLANT NAMED 'DLFLYCH7'**

(50) Latin Name: ***Chrysanthemum* X *morifolium***
Varietal Denomination: 'DLFLYCH7'

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/548,556

(22) Filed: Dec. 12, 2021

Related U.S. Application Data

(60) Provisional application No. 63/124,834, filed on Dec. 13, 2020.

(51) Int. Cl.
*A01H 5/02* (2018.01)
*A01H 6/14* (2018.01)

(52) U.S. Cl.
USPC ..... Plt./293

(58) Field of Classification Search
USPC ..... Plt./284, 286, 287, 293
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'DLFLYCH7', characterized by its upright plant habit; uniform growth habit; dark green-colored leaves; strong upright flowering stems; decorative-type inflorescences with purplish red-colored ray florets; resistance to *Fusarium* and Western Flower Thrips; relative tolerance to low production temperatures; and good postproduction longevity.

1 Drawing Sheet

Figure 1:
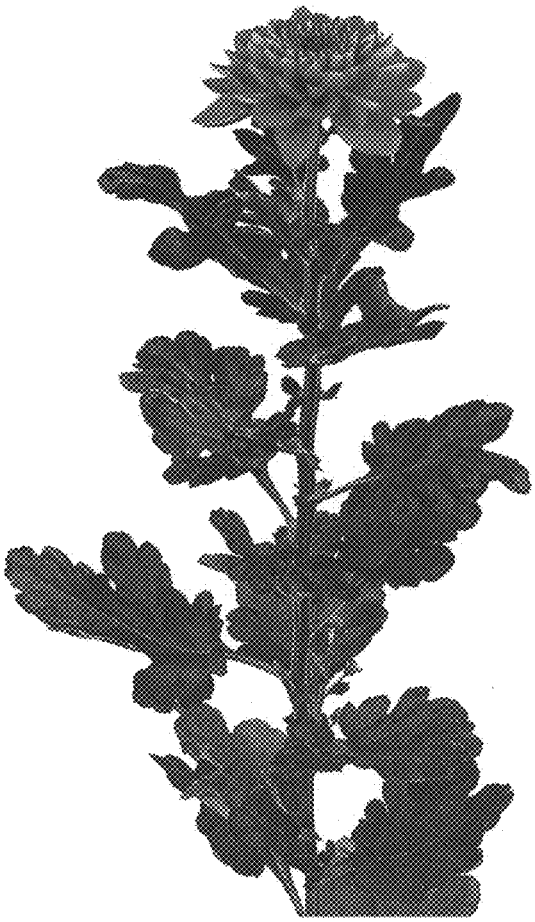

Botanical designation: *Chrysanthemum* X *morifolium*.
Cultivar denomination: 'DLFLYCH7'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Dec. 29, 2020, application number A202738. Foreign priority is not claimed to this application.

A Japanese Plant Breeder's Rights application for the instant plant was filed by the Assignee, Deliflor Royalties B.V. of Maasdijk, The Netherlands on Aug. 31, 2020, application number 34912. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFLYCH7'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in February, 2017 of a proprietary selection of *Chrysanthemum* x *morifolium* identified as code number db 33408, not patented, as the female, or seed, parent with a proprietary selection of *Chrysanthemum* x *morifolium* identified as code number db 42809, not patented, as the male, or pollen, parent. The new *Chrysanthemum* plant was discovered and selected as a single flowering plant from within the progeny of the stated cross-pollination in a controlled greenhouse environment in Maasdijk, The Netherlands in October, 2017.

Asexual reproduction of the new *Chrysanthemum* plant by vegetative terminal cuttings since October, 2017 in a controlled greenhouse environment in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFLYCH7'. These characteristics in combination distinguish 'DLFLYCH7' as a new and distinct *Chrysanthemum* plant:

1. Upright plant habit; uniform growth habit.
2. Dark green-colored leaves.
3. Strong upright flowering stems.
4. Decorative-type inflorescences with purplish red-colored ray florets.
5. Resistant to *Fusarium* (*Fusarium oxysporum*) and Western Flower Thrips.
6. Relatively tolerant to low production temperatures.
7. Good postproduction longevity.

Plants of the new *Chrysanthemum* differ primarily from plants of the female parent selection in ray floret color as ray florets of plants of the new *Chrysanthemum* are purplish red in color whereas ray florets of plants of the female parent selection are purplish pink in color. In addition, ray florets of plants of the new *Chrysanthemum* have more rounded apices than ray florets of plants of the female parent selection.

Plants of the new *Chrysanthemum* differ primarily from plants of the male parent selection in ray floret color as ray florets of plants of the new *Chrysanthemum* are purplish red in color whereas ray florets of plants of the male parent selection are red in color. In addition, ray florets of plants of the new *Chrysanthemum* are less carinate than ray florets of plants of the male parent selection.

Plants of the new *Chrysanthemum* can be compared to plants of *Chrysanthemum* X *morifolium* 'Delibarca Red', not patented. In side-by-side comparisons, plants of the new *Chrysanthemum* differ primarily from plants of 'Delibarca Red' in ray floret color as ray florets of plants of the new *Chrysanthemum* are purplish red in color whereas ray florets of plants of 'Delibarca Red' are deep red in color. In addition, ray florets of plants of the new *Chrysanthemum* have bluntly acute to obtuse apices whereas ray florets of plants of 'Delibarca Red' have mammillate apices.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFLYCH7' grown as a disbud-type cut flower.

Figure 2:
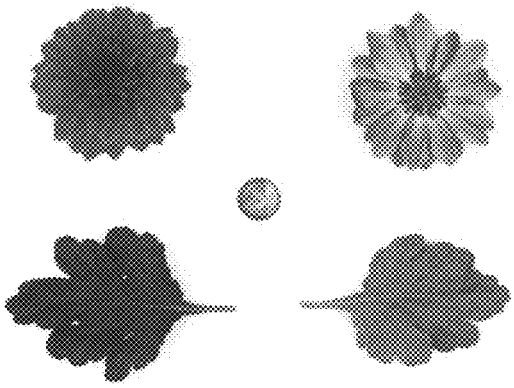

The photograph at the bottom of the sheet (FIG. 2) is a close-up view of upper (left) and lower (right) surfaces of typical inflorescences and typical leaves of 'DLFLYCH7'.

DETAILED BOTANICAL DESCRIPTION

The aforementioned photographs and following observations and measurements describe plants grown during the late winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 7 klux. Plants were grown as single-stem disbud-type plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFLYCH7'.

Parentage:

*Female, or seed, parent.*—Proprietary selection of *Chrysanthemum* x *morifolium* identified as code number db 33408, not patented.

*Male, or pollen, parent.*—Proprietary selection of *Chrysanthemum* x *morifolium* identified as code number db 42809, not patented.

Propagation:

*Type.*—Terminal vegetative cuttings.

*Time to initiate roots, summer.*—About four days at temperatures about 20° C.

*Time to initiate roots, winter.*—About six days at temperatures about 20° C.

*Time to produce a rooted young plant, summer.*—About 13 days at temperatures about 20° C.

*Time to produce a rooted young plant, winter.*—About 15 days at temperatures about 20° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous decorative-type cut flower that is typically grown as a single stem disbud-type; upright plant habit; vigorous growth habit and rapid growth rate.

*Plant height, soil level to top of foliar plane.*—About 66.4 cm.

*Plant height, soil level to top of inflorescence plane.*—About 73 cm.

*Plant (spray) diameter.*—About 20.3 cm.

*Flowering stem length.*—About 60.6 cm.

*Flowering stem diameter.*—About 7 mm.

*Flowering stem internode length.*—About 2.7 cm.

*Flowering stem strength.*—Strong.

*Flowering stem aspect.*—Erect.

*Flowering stem texture and luster.*—Moderately pubescent; slightly glossy.

*Flowering stem color, developing.*—Close to 143B.

*Flowering stem color, developed.*—Close to 146A; at the ridges, close to 146B.

*Leaf description.*—Arrangement: Alternate; simple. Length: About 11.4 cm. Width: About 7.9 cm. Shape, in overall outline: Broadly ovate to broadly oblong. Apex: Abruptly acute, minute. Base: Attenuate. Margin: Palmately lobed, coarsely crenate; sinuses parallel to convergent and medium to deep in depth; moderately undulate. Texture and luster, upper surface: Sparsely pubescent, not rugose; moderately velvety; slightly glossy. Texture and luster, lower surface: Moderately pubescent, prominent venation; slightly velvety; matte. Venation pattern: Pinnate, reticulate. Color: Developing leaves, upper surface: Close to 137A. Developing leaves, lower surface: Close to 147B. Fully developed leaves, upper surface: Close to NN137A; venation, close to 146B. Fully developed leaves, lower surface: Close to 147B; venation, close to 146C. Petioles: Length: About 1.8 cm. Diameter: About 3 mm by 4 mm. Strength: Moderately strong. Texture and luster, upper and lower surfaces: Densely pubescent; moderately glossy. Color, upper and lower surfaces:

Close to 146C; edges, close to 143A. Stipules: Quantity and appearance: Two leafy stipules, opposite, at the petiole attachment to the stem. Length: About 1.1 cm. Width: About 1.7 cm. Shape, in overall outline: Roughly reniform; apex, emarginate to cleft; base, broadly cuneate. Texture and luster, upper surface: Sparsely pubescent; slightly glossy. Texture and luster, lower surface: Moderately pubescent; matte. Color, upper surface: Close to NN137A. Color, lower surface: Close to 147B.

Inflorescence description:

*Appearance.*—Decorative-type inflorescence form with flat to recurved obovate-shaped ray florets and tubular disc florets; inflorescences borne perpendicular to peduncles and face upright; ray and disc florets develop acropetally on a capitulum.

*Fragrance.*—Faintly fragrant; typical of *Chrysanthemums.*

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 59 days later when grown as a disbud-type.

*Postproduction longevity.*—Good postproduction longevity; after a seven-day storage period, cut flowers will maintain good color and substance for about two weeks in an interior environment; inflorescences persistent.

*Quantity of inflorescences.*—Typically grown as a disbud-type, only the terminal inflorescence is allowed to developed; if grown as a spray-type, about 15 inflorescences develop per flowering stem.

*Inflorescence size.*—Diameter, grown as a disbud-type: About 8.9 cm. Depth (height), grown as a disbud-type: About 9 cm. Diameter, grown as a spray-type: About 5 cm. Depth (height), grown as a spray-type: About 8.2 cm. Disc diameter: About 5 mm.

*Receptacles.*—Height: About 9 mm. Diameter: About 1.4 cm. Shape: Flattened globular. Color: Close to 145C.

*Inflorescence buds.*—Height: About 9 mm. Diameter: About 1.2 cm. Shape: Hemispherical. Texture and luster: Densely pubescent; matte. Color: Developing involucral bracts, close to 137A and 138B to 138C; developing ray florets, close to 157A.

*Ray florets.*—Quantity and arrangement: About 300 arranged in about eight whorls. Length: About 4.2 cm, varying between 3.9 cm and 4.5 cm. Width: About 1.6 cm, varying between 1.4 cm and 1.8 cm. Shape: Obovate; mostly flat and slightly carinate; moderately recurved. Apex: Bluntly acute to obtuse. Base: Attenuate. Margin: Entire; proximally, undulate. Aspect: About 55° from vertical. Texture and luster, upper surface: Smooth, glabrous; moderately velvety; matte. Texture and luster, lower surface: Smooth, glabrous; slightly velvety; slightly glossy. Color: When opening, upper surface: Close to 61A; towards the base, close to 64A and at the base, close to 157D. When opening, lower surface: Close to 76A to 76D; towards the base, close to 150C. Fully opened, upper surface: Close to 64B; towards the apex, close to 64A and towards the base, close to 150C; venation, similar to lamina colors; color does not change with subsequent development. Fully opened, lower surface: Close to 75B; towards the base, close to 76D and at the base, close to 1B; venation, similar to lamina colors; color does not change with subsequent development.

*Disc florets.*—Quantity and arrangement: About 15 randomly arranged at the center of the receptacle. Length: About 1 cm. Diameter: About 3 mm. Shape: Tubular; proximally, 90% fused and distally, 10% free. Apex: Acute. Margin, free-part: Entire. Texture and luster, inner and outer surfaces: Smooth, glabrous; glossy. Color: When developing and fully developed, inner surface: Towards the apex, close to 2A; mid-section, close to 1C and towards the base, close to 145D. When developing and fully developed, outer surface: Towards the apex, close to 2A; mid-section, close to 1C and towards the base, close to 145D.

*Involucral bracts.*—Quantity and arrangement: About 30 arranged in about two whorls. Length: About 1 cm. Width: About 4 mm. Shape: Oblong to ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to a blend of 143A to 146B; lateral margins, translucent and close to 145D and 157A and apical margins tinged with close to N199A. Color, lower surface: Close to a blend of 137B and 144A; lateral margins, translucent and close to 145D and 157A and apical margins tinged with close to N199A.

*Peduncles.*—Length, terminal peduncle: About 8.5 cm. Diameter, terminal peduncle: About 4 mm. Length, third peduncle, grown as a spray-type: About 8.9 cm. Diameter, third peduncle, grown as a spray-type: About 3 mm. Strength: Strong. Aspect, terminal peduncle: Upright. Aspect, third peduncle, grown as a spray-type: About 40° from the flowering stem axis. Texture and luster: Densely pubescent; moderately glossy. Color: Close to 143A; at the ridges, close to 143B.

*Reproductive organs.*—Androecium: Present on disc florets only. Quantity: About five per floret. Filament length: About 4 mm. Filament color: Close to 154C. Anther size: About 0.5 mm by 2 mm. Anther shape: Oblong. Anther color: Close to 161A. Pollen amount: None observed. Gynoecium: Present on both ray and disc florets. Quantity: One per floret. Pistil length: About 9 mm. Style length: About 8 mm. Style color: Close to 150C. Stigma diameter: About 1.5 mm. Stigma shape: Cleft, decurrent. Stigma color: Close to 151B. Ovary color: Close to 157A.

*Seeds and fruits.*—To date, seed and fruit development have not been observed on plants of the new *Chrysanthemum.*

Pathogen & pest resistance: Plants of the new *Chrysanthemum* have been observed to be resistant to *Fusarium* (*Fusarium oxysporum*) and Western Flower Thrips. To date, plants of the new *Chrysanthemum* have not been observed to be resistant to other pathogens and pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFLYCH7' as illustrated and described.

* * * * *